(12) United States Patent
Wohlfarth

(10) Patent No.: US 8,280,487 B2
(45) Date of Patent: Oct. 2, 2012

(54) METHOD AND APPARATUS FOR AUTOMATICALLY CONTROLLING TABLETOP DISPLACEMENT IN MAGNETIC RESONANCE IMAGING

(75) Inventor: Katrin Wohlfarth, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1269 days.

(21) Appl. No.: 11/673,274

(22) Filed: Feb. 9, 2007

(65) Prior Publication Data

US 2007/0232895 A1    Oct. 4, 2007

(30) Foreign Application Priority Data

Feb. 10, 2006  (DE) .................. 10 2006 006 309

(51) Int. Cl.
*A61B 5/05* (2006.01)
(52) U.S. Cl. ............ 600/415; 600/410; 5/601; 324/306; 324/307; 324/309
(58) Field of Classification Search .................. 600/410, 600/415; 5/601; 324/306, 307, 309
See application file for complete search history.

(56) References Cited

U.S. PATENT DOCUMENTS

| | | | |
|---|---|---|---|
| 5,928,148 A * | 7/1999 | Wang et al. ................... | 600/420 |
| 6,195,409 B1 | 2/2001 | Chang et al. | |
| 6,529,762 B1 | 3/2003 | Ladebeck | |
| 7,486,076 B2 * | 2/2009 | Nagao et al. .................. | 324/318 |
| 2002/0087066 A1 | 7/2002 | Hellinger | |
| 2003/0098688 A1 | 5/2003 | Brinker et al. | |
| 2004/0207401 A1* | 10/2004 | Kirsch .......................... | 324/306 |
| 2005/0088177 A1 | 4/2005 | Schreck et al. | |
| 2005/0171423 A1* | 8/2005 | Ho et al. ....................... | 600/410 |
| 2007/0016001 A1 | 1/2007 | Graf | |

* cited by examiner

*Primary Examiner* — Brian Casler
*Assistant Examiner* — Joseph M Santos
(74) *Attorney, Agent, or Firm* — Schiff Hardin LLP

(57) ABSTRACT

In a method for operation of a magnetic resonance apparatus having a patient positioning table with a tabletop as well as a control device by which the displacement of the tabletop relative to a homogeneous magnetic field (generated by a magnetic field generation device) and the acquisition of images of an anatomical subject of the patient in a field of view within the homogeneous magnetic field are controlled, the control device determines a suitable stepped displacement of the tabletop using information about the patient size, information about the subject to be acquired and information about the size of the homogeneous magnetic field and/or field of view present relative to the table displacement direction, and the control device controls the tabletop displacement as needed according to the determination result.

10 Claims, 1 Drawing Sheet

Magnetic Field Generation Device
Position Marker
Monitor
Positioning Table
Control Device
Input Device

METHOD AND APPARATUS FOR AUTOMATICALLY CONTROLLING TABLETOP DISPLACEMENT IN MAGNETIC RESONANCE IMAGING

BACKGROUND OF THE INVENTION

1. Field of the Invention

The present invention concerns a method for operating a magnetic resonance apparatus having a patient positioning table with a tabletop as well as a control device, with which the displacement of the tabletop relative to a homogeneous magnetic field (generated by a magnetic field generation device) and the acquisition of images of an anatomical subject of the patient in a field of view within the homogeneous magnetic field are controlled.

2. Description of the Prior Art

A magnetic resonance apparatus serves for the acquisition of images of a patient that for this purpose is exposed to a homogeneous magnetic field. Radio-frequency magnetic fields, and gradient fields for spatial resolution, are superimposed on this homogeneous magnetic field in order to be able to acquire spatially-resolved resonance signals and generate corresponding images of the examination region therefrom. The basic operation of a magnetic resonance apparatus is well known and need not be described in detail herein.

Because increasingly shorter magnets are used, for the acquisition of anatomical subjects of a patient that are longer than the homogeneous magnetic field or the field of view within the homogeneous magnetic field, the patient lying within the homogeneous magnetic field and within whom the images are acquired, it is typical to move the patient through the magnet (consequently thus to move the homogeneous magnetic field) by suitable table displacement and to acquire the images in various positions, known as levels. The individual various image sets or slice sets that are acquired at the respective table position overlap one another at the edges, such that they can be fused to generate an overall image or a contiguous slice exchange. A typical example is the acquisition of an image of the spinal column that, for example, is approximately 80-90 cm long in adults while the homogeneous magnetic field (known as the homogeneity volume) is typically, maximally approximately 50 cm large while the field of view is sometimes even smaller (depending on the selected measurement sequence), for example only 40 cm with regard to the Z-direction of the magnetic field (corresponding to the movement direction of the patient table).

The user conventionally has to control the table displacement himself or herself, as well as having to define the control parameters. This means that the user had to define the table positions to be acquired, at which table positions the individual slice image stacks are acquired with regard to the length (for example of the spinal column). The user must establish how large the overlap region of the adjoining individual images should be, how large the length of the organ to be acquired, which specific measurement sequence should be selected, dependent on which the field of view possibly changes etc. The user is thus required to employ a number of considerations in order to subsequently, quasi-manually operate the control device. This is laborious and time-consuming; possible errors sometimes lead to incomplete or unusable images.

SUMMARY OF THE INVENTION

An object of the present invention is to provide a method for operation of a magnetic resonance apparatus that is improved in this regard and unburdens the user.

This object is achieved in accordance with the invention by a method of the aforementioned type wherein the control device determines a suitable stepped displacement of the tabletop using information about the patient size, information about the subject to be acquired and information about the size of the homogeneous magnetic field and/or field of view present with regard to the table displacement direction and, as needed, the control device controls the tabletop displacement according to the determination result.

According to the invention the determination of a suitable stepped table displacement ensues automatically on the part of the control device using three parameters or, items of information, namely information about the patient size, information about the subject to be acquired (for example, the spinal column or the femur) as well as information about the size of the homogeneous magnetic field or field of view, depending on what is most appropriate for table displacement calculation with regard to the upcoming image acquisition.

From the information about the patient size as well as the information about the subject to be acquired, the control device can immediately derive the size of the subject to be acquired. For example, the spinal column of a child is distinctly smaller than that of an adult. From the information about the patient size (for example 185 cm) as well as the information about the organ to be acquired (for example, the spinal column), the control device immediately "knows" that the spinal column possesses a length of approximately 80 cm. Using the information about the size of the homogeneous magnetic field/field of view, information about the dimension of the displayable slice (consequently thus the length or, respectively, coverage of the spinal column that can be shown in an image) is furthermore available to the control device. If a homogeneity volume of, for example, 50 cm and a spinal column length of 80 cm are assumed, for example, a complete coverage of the spinal column (consequently thus a complete acquisition of the spinal column) would be possible over two adjoining image sequences, with the individual images or slice images overlapping by, for example, 5 cm. The control device thus determines that only two defined tabletop positions in which the corresponding slice image stacks are acquired must be occupied. Naturally, depending on the embodiment one acquisition in three varying table positions can also ensue instead of two adjoining image sequences. This is possible, for example, given a shorter field of view of, for example, 40 cm. Here as well a sufficient overlap also exists in the Z-direction (in the longitudinal direction through the magnetic generation device). Here the control device would determine three dedicated table positions to be occupied, in which table positions the image acquisitions ensue.

In each case the determination of the table displacement (and along with this the individual table positions to be occupied insofar as a table displacement with regard to the organ to be acquired is required at all) ensues solely on the part of the control device. For this purpose, the user is only to the extent of possibly having to input the one or more items of information. The previous user-controlled determination that is time-consuming and consequently error-prone is advantageously no longer required.

As stated, the user may still be required to possibly define (by a suitable input) information that the control device needs for automatic determination of the table displacement. The user must typically define at least the subject of the patient to be acquired, for example just the spinal column, or a leg, etc. The user can likewise manually enter information about the body size; the corresponding patient information is typically present. Alternatively, it is possible for this information to be automatically detected by the magnetic resonance apparatus.

For this purpose, the magnetic resonance apparatus acquires, for example, a whole-body overview image of the patient. Controlled by the control device, the patient is moved once completely through the magnetic resonance apparatus by the patient positioning table so that a whole-body overview image can be acquired. Using this information the control device can determine, for example, the patient size (consequently thus automatically detect this information) without further measures by means of a suitable image analysis. The information about the size of the homogeneity volume is present anyway at the control device as one of the central operating parameters of the magnetic resonance apparatus, as well as the information about the size of the field of view which possibly changes dependent on the measurement sequence selected by the user. In each case this information is likewise present at the control device. The control device can now define the table displacement without further measures using the additional information provided by the user about the subject to be acquired.

Information defining a table position adopted for the beginning of the image acquisition is appropriately taken into account in the determination of the table displacement. This can either be manually input by the user, for which the user moves the patient table together with the patient into an appropriate position that should be adopted as a first start position with the beginning of the image acquisition. This position can be defined, for example, using optical light markings. For a spinal column acquisition the patient is typically positioned such that the larynx is positioned in the middle of the homogeneity volume and that in the middle of the field of view. In addition to such a manual start position determination, it is also possible for this start position to be automatically determined by an image analysis, in particular using the overview image, such as in connection with the information already provided about the subject to be acquired.

Furthermore, the determination of the table displacement can ensue by taking into account the measurement sequence selected by the user. The user can select different measurement sequences that supply different image information and thus different diagnostic information from the examination subject. The measurement sequences can differ with regard to the sensitivity of the signal acquisition from the homogeneity volume. While some measurement sequences react to the slightest magnetic field inhomogeneities (consequently, given a homogeneity volume of the basic magnetic field of, for example, 50 cm, a maximum field of view of, for example, only 40 cm or less offers the required homogeneity criteria for the signal acquisition), in contrast to this other measurement sequences are significantly less sensitive so that the entire homogeneity volume (thus the homogeneous basic magnetic field) can be used as the field of view. The basic magnetic field or, respectively, homogeneity volume of the basic magnetic field is defined as the magnetic field volume within which the magnetic field invariance is smaller than a liquid volume. The term of "the homogeneous magnetic field" or "homogeneity volume" is well known to those skilled in the art.

In each case a possible dependency of the image acquisition on the measurement sequence-dependent field of view is taken into account in the inventive method. If the user thus selects a "sensitive" measurement sequence with a field of view that is distinctly smaller than the homogeneity volume, the size of the field of view is thus taken into account in the displacement determination in connection with the requested overlap. This can lead to the situation that, for example, three table positions are required for complete subject coverage given a first acquisition (of, for example, the spinal column) with such a measurement sequence while only two table positions are to be occupied for complete coverage given a subsequent acquisition with a different "insensitive" measurement sequence.

An "insensitive" sequence is, for example, a spin echo sequence. This is barely sensitive to field inhomogeneities since here a 180° RF refocusing pulse which reverses the dephasing is switched.

An example of a "sensitive" sequence is a gradient echo sequence. This is susceptibility-sensitive since, due to the lack of a 180° RF refocusing pulse, it leads to dephasings as a consequence of T2 decay, magnetic field inhomogeneities and susceptibility. This leads to a signal loss at tissue-air transitions and to distortions as a result of field inhomogeneities.

In addition to the size of the field of view (which is dependent on the selected measurement sequence), a possible dependency of the required overlap region on the selected measurement sequence should also be taken into account given the determination of the table positions. A sequence that reacts more sensitively to inhomogeneities at the edge of the homogeneous magnetic field requires a larger overlap region than a sequence reacting relatively insensitively to boundary inhomogeneities.

In an embodiment the control device varies the size of the field of view using a measurement sequence selected by the user. If, for example, an "insensitive" measurement sequence is selected that enables a barely-possible coverage of the subject in two table positions, according to this embodiment of the invention it is possible for the field of view to be reduced and (under consideration of the required overlap) three table positions (consequently thus three slice image stacks at these table positions) are acquired. The reduction of the field of view leads to an improved resolution of the acquired images, which is appropriate in may cases.

In addition to varying the size of the field of view dependent on the selected measurement sequence, or alternatively thereto it is also possible for the control device to determine the field of view dependent on the size of the subject to be acquired. For example, if the femur should be acquired (the femur is, for example, 60 cm long in an adult, or relative to the input patient size), given a size of the homogeneity volume (homogeneous magnetic field) of 50 cm it is required to take up two table positions for image acquisition. Nevertheless it is sufficient to reduce the field of view to, for example, 40 cm since a sufficient coverage can always still be achieved given an existing overlap.

Finally, the determination of the table displacement can ensue by taking into account manually-input or automatically-selected information concerning the overlap of two adjacent images of the subject. This means that a certain variation possibility for the user or the control device itself also exists with regard to this parameter that enters into the determination of the table displacement.

The invention also concerns a magnetic resonance apparatus having a patient positioning table with a tabletop as well as a control device via which the displacement of the tabletop relative to a homogeneous magnetic field (which can be generated by the magnetic field generation device) and the acquisition of images of an anatomical subject of the patient in a field of view within the magnetic field can be controlled. The magnetic resonance apparatus or control device is fashioned for implementation of the described method.

DESCRIPTION OF THE PREFERRED EMBODIMENTS

Figure 1:
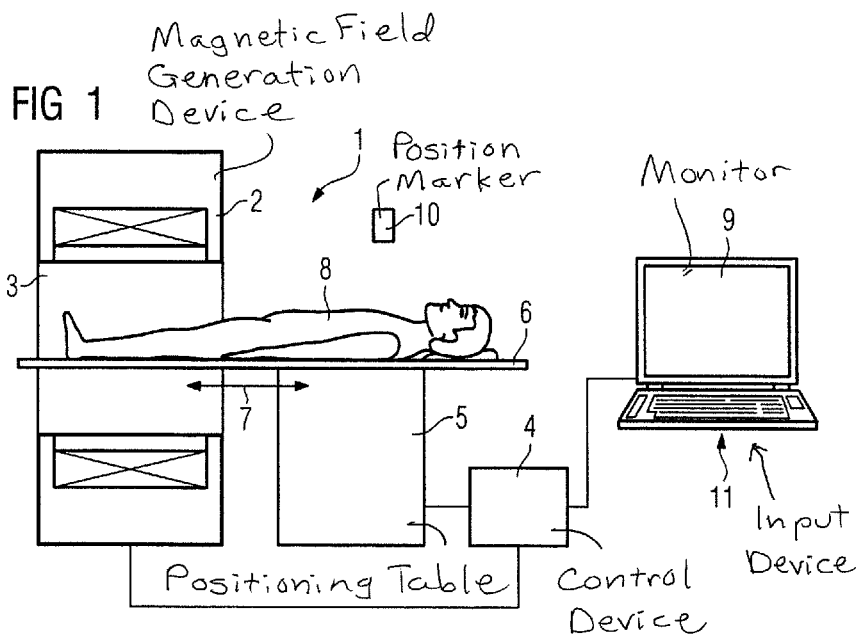
FIG. 1 is a basic representation of an inventive magnetic resonance apparatus suitable for implementation of the inventive method.
Figure 2:
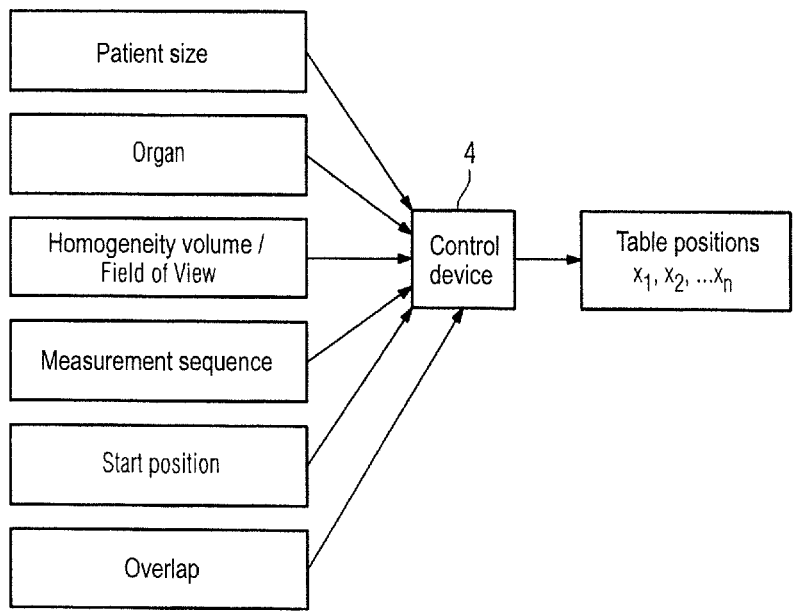
FIG. 2 is a diagram showing the various items of information/parameters for determination of the table positions to be adopted.

FIG. 1 shows an inventive magnetic resonance apparatus 1 having a magnetic field generation device 2 with which a homogeneous magnetic field (homogeneity volume) is generated in the examination volume 3 of the magnetic resonance apparatus 1. The operation of the magnetic field generation device 2 is controlled by a control device 4. The magnetic field generation device 2 furthermore has a coil system for generation of gradient fields as well as a radio-frequency magnetic field, which is, however, not discussed in detail. The basic design of a magnetic resonance apparatus is known to those skilled in the art and need not be explained in detail herein.

Also provided is a patient positioning table 5 with a tabletop 6 that, as shown by the arrow 7, can be longitudinally displaced such that a patient 8 can be moved through the examination volume 3 (consequently through the homogeneous magnetic field). If an image of an object in the patient 8 should also be acquired, it is positioned by the displaceable tabletop 6 such that the subject to be acquired lies inside the examination volume 3, consequently inside the homogeneity volume. The measurement sequences selected for image acquisition are subsequently executed, meaning that the control device 4 controls the magnetic field generation device 2. The acquired image signals are provided to the control device 4 in a known manner, and the control device 4 then generates corresponding images that are output on a monitor 9.

If a subject (such as, for example, the spinal column) should be acquired that is unavoidably, distinctly longer than the homogeneity volume or the field of view situated within this homogeneity volume, a number of positions in which corresponding images are acquired are acquired by the tabletop 6. These images are subsequently merged by the control device 4 into an image exposure showing the entire subject (here the spinal column) and output on a monitor 9.

Furthermore, a specific start position in which the image acquisition has to begin can be defined via a position marker 10. This selected start position is communicated to the control device 4.

In the inventive magnetic resonance apparatus or the inventive method, the control device 4 is now designed for automatic determination of the possible table displacement or, respectively, table positions to be adopted that are required depending on the anatomical subject of the patient 8 that is to be acquired.

At the beginning of the examination the user initially inputs the patient size of the patient 8 (for example 185 cm) via a suitable input device 11 (here, for example, a keyboard). In connection with the selected subject, the subject size can always also be concluded from the patient size. The user subsequently selects (for example via corresponding image representations or icons on the monitor 9) the organ to be acquired (for example the spinal column). These items of information are provided to the control device 4. The size of the homogeneity volume or of the field of view (thus the region within the homogeneity volume within which diagnostically suitable images can be acquired) is also known to the control device 4 as a device-immanent parameter. For example, a typical homogeneity volume size is 50 cm (the homogeneity volume is approximately a sphere; the size would be the sphere diameter). In many measurement sequences the size of the homogeneity volume also corresponds to the field of view.

These three parameters "patient size", "organ", "homogeneity volume/field of view" are the three central items of basic information that the control device 4 requires in order to determine the corresponding table positions to be taken up in succession that serve for image acquisition and complete coverage of the organ. These table positions are specified as $x_1, x_2, \ldots, x_n$.

As stated, the user can input the patient size. Alternatively, it is also possible for the control device 4 to determine this itself. For this purpose, a whole-body overview image is initially acquired. The control device 4 controls the tabletop movement such that the entire length of the patient is initially moved through the magnetic resonance apparatus 1 and a whole-body overview image is thereby acquired, which whole-body overview image thus shows the patient over his entire length. Using this image, the control device 4 can now determine the feet and head ends of the patient and the patient size resulting from this without further measures, and consequently can automatically generate this information.

The information about the measurement sequence selected by the user is appropriate as further optional information that can be processed for definition of the individual table positions. Different measurement sequences that lead to the acquisition of different image signals (and consequently different image information) can be selected. Some measurement sequences work only with a limited field of view, meaning that the maximum allowable length of the field of view is possibly varied dependent on the respective measurement sequence. It naturally, inevitably results from this that the coverage of the organ (consequently thus the number of the images to be acquired in succession) is different. Given a small field of view, more images are inevitably to be appended to one another in order to cover the entire subject. The control device is now able to determine the corresponding allowable field of view from the selected measurement sequence and, under consideration of this information, to define the table positions to be occupied.

Further information that can possibly be manually input by the user is the overlap. The images to be joined to form an overall representation always overlap to a certain degree such that the images can be fused with accurate position. This degree of overlap can possibly be varied, either by manual definition by the user, or by a fixed overlap parameter.

Furthermore, information about the start position is to be taken into account on the part of the control device 4. The start position, thus the first table position $x_1$ that is to be taken up and in which the first image acquisition ensues, can be defined by the user (for example in connection with the position marker 10). This position marker 10 (for example a light beam localizer) is positionally stable; the patient 8 is correspondingly aligned with regard to the position marker 10 for determination of the start position. The determination of the further table positions $x_2, \ldots$, then ensues starting from this selected start position under consideration of the further discussed information. For example, if the spinal column should be acquired, the user defines the larynx of the patient by the position marker, meaning that the patient is positioned such that the position marker (thus, for example, the light beam localizer) marks the larynx. Starting from this defined start position (in which here the cervical vertebrae can be acquired), the further positions to be taken up are determined under consideration of the cited parameters in order to acquire the thoracic vertebrae and the lumbar vertebrae. For image acquisition the patient is then positioned by the table displacement such that the larynx marked previously is in the middle of the homogeneity volume or, respectively, the field of view, which is the case upon reaching the start position. The image acquisition then ensues in this position; the second position is subsequently taken up and so forth. As soon as the position marker is centrally (with regard to the homogeneity volume or, respectively, the field of view) arranged inside the bore of the magnetic resonance apparatus, the patient is already located in the first acquisition position at the point in time of the marking, such that only the following [sic] is still to be taken up.

Moreover, the control device is also fashioned such that the field of view can be varied, meaning that if necessary the position determination is to be based on a small field of view insofar as this is appropriate using the given information about patient size, organ, measurement sequence and overlap. An improvement of the resolution can be achieved by a reduction of the field of view; depending on the present clinical question, or thus the organ to be acquired, it is, for example, sometimes appropriate to image this not in two levels (thus table positions to be taken up) but rather in three.

Although modifications and changes may be suggested by those skilled in the art, it is the intention of the inventor to embody within the patent warranted hereon all changes and modifications as reasonably and properly come within the scope of her contribution to the art.

I claim as my invention:

1. A method for operating a magnetic resonance apparatus, said magnetic resonance apparatus comprising a magnetic field generator that generates a homogenous magnetic field, a patient positioning table having a displaceable tabletop, and a control device that controls displacement of said tabletop relative to the homogenous magnetic field for acquisition of images of an anatomical object of the patient in a field of view within said homogenous magnetic field, said method comprising the steps of:
    making information accessible by said control device that describes a size of the patient, identifies said anatomical object, and describes a size of said homogenous magnetic field in a direction corresponding to a direction of displacement of said tabletop;
    in said control device, automatically, non-manually determining a size of the anatomical object from said size of the patient, and automatically, non-manually determining a determined size of said field of view dependent on said size of said anatomical object;
    in said control device, automatically, non-manually determining a stepped displacement of said tabletop from said determined size of said field of view and said size of said anatomical object, and configuring said stepped displacement to acquire data from a plurality of successive regions of the patient with respective adjoining regions in said successive regions exhibiting an overlap with each other in order to acquire image data from the patient with complete coverage of said anatomical object;
    making further information accessible by said control device that identifies a data acquisition protocol to be used for said image data acquisition and, in said control unit, automatically, non-manually adjusting said determined size of said field of view dependent on said image acquisition protocol, to obtain an adjusted size of said field of view and also automatically, non-manually determining a final stepped displacement for said tabletop in said image data acquisition, with said overlap, dependent on said adjusted size of said field of view, that maintains said complete coverage of said anatomical object; and
    from said control unit, operating said magnetic resonance apparatus to acquire said image data from said patient on said tabletop with said tabletop being displaced by said final stepped displacement.

2. A method as claimed in claim 1 comprising making said information describing said size of said patient accessible by said control device by a manual input into said control device.

3. A method as claimed in claim 1 comprising making said information describing said size of said patient accessible by said control device by obtaining an overview image exposure of said patient and automatically making said overview image exposure of said patient accessible by said control device.

4. A method as claimed in claim 1 comprising making additional information accessible by said control device defining a position of said tabletop to be adopted at a beginning of said image data acquisition and comprising, in said control device, automatically electronically determining said stepped displacement on said information and said additional information.

5. A method as claimed in claim 4 comprising making said position of said tabletop to be adopted at the beginning of said image data acquisition accessible by said control device by a manual input into said control device.

6. A method as claimed in claim 4 comprising making said position of said tabletop to be adopted at the beginning of said image data acquisition accessible by said control device by automatically determining said position of said tabletop to be adopted at the beginning of the image data acquisition in said control device.

7. A method as claimed in claim 1 comprising making additional information accessible by said control device describing a selected measurement sequence for obtaining said image data in said image data acquisition, and comprising, in said control device, automatically electronically determining said stepped displacement dependent on said information and said additional information.

8. A method as claimed in claim 1 comprising manually entering into said control unit information describing said overlap.

9. A method as claimed in claim 1 comprising, also non-manually, automatically adjusting a size of said overlap in determining said stepped displacement.

10. A magnetic resonance apparatus comprising:
    a magnetic resonance data acquisition unit comprising a magnetic field generator that generates a homogenous magnetic field;
    a patient positioning table having a displaceable tabletop; and
    a control device provided with information that describes a size of the patient, identifies said anatomical object, and describes a size of said homogenous magnetic field in a direction corresponding to a direction of displacement of said tabletop;
    said control device being configured to automatically determine a size of the anatomical object from said size of the patient, and automatically determine a determined size of said field of view dependent on said size of said anatomical object;
    said control device being configured to automatically determine a stepped displacement of said tabletop from said determined size of said field of view and said size of said anatomical object, and to configure said stepped displacement to acquire data from a plurality of successive regions of the patient with respective adjoining regions in said successive regions exhibiting an overlap with each other in order to acquire image data from the patient with complete coverage of said anatomical object;

said control device being provided with further information that identifies a data acquisition protocol to be used for said image data acquisition, and said control unit being configured to automatically adjust said determined size of said field of view dependent on said image acquisition protocol, to obtain an adjusted size of said field of view and to also automatically determine a final stepped displacement for said tabletop in said image data acquisition, with said overlap, dependent on said adjusted size of said field of view, that maintains said complete coverage of said anatomical object; and said control unit being configured to operate said magnetic resonance apparatus to acquire said image data from said patient on said tabletop with said tabletop being displaced by said final stepped displacement.

* * * * *